US006605734B2

(12) United States Patent
Roy et al.

(10) Patent No.: US 6,605,734 B2
(45) Date of Patent: Aug. 12, 2003

(54) ALKENE-PLATINUM-SILYL COMPLEXES

(75) Inventors: Aroop Kumar Roy, Midland, MI (US); Richard Bruce Taylor, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/017,229

(22) Filed: Dec. 7, 2001

(65) Prior Publication Data
US 2003/0109732 A1 Jun. 12, 2003

(51) Int. Cl.[7] .............. C07F 19/00; C07F 7/00; C07F 15/00; B01J 31/00
(52) U.S. Cl. .............. 556/9; 556/12; 556/479; 556/465; 502/152; 502/158
(58) Field of Search .............. 556/9, 12, 479, 556/465; 502/152, 158

(56) References Cited

U.S. PATENT DOCUMENTS

| 4,292,434 | A | | 9/1981 | Lindner et al. ............. 556/479 |
|---|---|---|---|---|
| 4,695,643 | A | * | 9/1987 | Oertle et al. ............. 556/428 |
| 5,874,603 | A | * | 2/1999 | Arkles ............. 556/465 |
| 6,359,161 | B2 | | 3/2002 | Tonomura et al. .......... 556/479 |
| 6,388,119 | B1 | | 5/2002 | Bauer et al. ............. 556/479 |

FOREIGN PATENT DOCUMENTS

| EP | 0785202 | 7/1997 | ............. C07F/7/14 |
|---|---|---|---|
| EP | 0785204 | 7/1997 | ............. C07F/7/14 |
| EP | 0850943 | 7/1998 | ............. C07F/7/14 |

OTHER PUBLICATIONS

Roy, Aroop et al., "The First Alkene–Platinum–Silyl Complexes", Journal of the American Chemical Society, 2002, 124(32), 9510–9524, XP002232244.

Koplova L I et al., "Complexes of Platinum (II) in the Hydrosilylation of Unsaturated Compounds.", Russian ournal of General chemistry, Consultants Bureau, US., vol. 63, No. 6, part 1, Jun. 1, 1993, pp. 900–903, XP000440803.

J. American Chemical Society 1986, 108, 7228–7231, "Platimun–Catalyzed Hydrosilylation–Colloid Formation as the Essential Step." Lewis et al.

* cited by examiner

Primary Examiner—Porfirio Nazario-Gonzalez
(74) Attorney, Agent, or Firm—Patricia M. Scaduto

(57) ABSTRACT

Alkene-platinum-silyl complexes described by formula $(COD)Pt(SiR^1{}_{3-n})_2Y_n$ are claimed, where each $R^1$ is independently selected from organic groups, halo atoms, and siloxy groups, each Y is an independently selected divalent bridging group between the silicon atoms bonded to platinum, n is 0, 1, 2, or 3, and COD is 1,5-cyclooctadiene.

18 Claims, No Drawings

ALKENE-PLATINUM-SILYL COMPLEXES

FIELD OF THE INVENTION

The present invention relates to alkene-platinum-silyl complexes described by formula (I) $(COD)Pt(SiR^1{}_{3-n})_2Y_n$, where each $R^1$ is independently selected from organic groups, halo atoms, and siloxy groups, each Y is an independently selected divalent bridging group between the silicon atoms bonded to platinum, n is 0, 1, 2, or 3, and COD is 1,5-cyclooctadiene.

BACKGROUND OF THE INVENTION

Platinum compounds and complexes are well known catalysts for organic reactions, such as hydrosilation (or hydrosilylation), generally in amounts 5 to 100 parts per million mol per mol non-aromatic, multiple bond. Many so-called homogeneous platinum hydrosilation catalysts including the well-known Speier's Catalyst and Karstedt's Catalyst, though widely used, suffer from one or more disadvantages, such as loss of active platinum via precipitation at higher temperatures, slow catalysis rates for bulky or deactivated alkenes and concurrent side reactions, such as isomerization of the olefin. It is therefore desirable to find platinum hydrosilation catalysts that overcome one or more of the above disadvantages suffered by many known general purpose catalysts, and are also readily prepared, relatively inexpensive, and can provide high rates of reaction. A further positive attribute in such catalysts would be the ability to reuse the initial charge of catalyst without loss of activity, since platinum is a rare and precious metal with very low natural abundance.

The inventors have now discovered novel alkene-platinum-silyl complexes which are highly active catalysts and meet the above desirable qualities of robustness, homogeneity, ready synthesizability and maintenance of activity for repeated use.

SUMMARY OF THE INVENTION

The present invention is a class of alkene-platinum-silyl complexes described by formula (I)

$$(COD)Pt(SiR^1{}_{3-n})_2Y_n,$$

where each $R^1$ is independently selected from organic groups, halo atoms, and siloxy groups, each Y is an independently selected divalent bridging group between the silicon atoms bonded to platinum, n is 0, 1, 2, or 3, and COD is 1,5-cyclooctadiene. A method of making these complexes is also described.

DETAILED DESCRIPTION OF THE INVENTION

The present invention is a class of alkene-platinum-silyl complexes described by formula (I)

$$(COD)Pt(SiR^1{}_{3-n})_2Y_n,$$

where each $R^1$ is independently selected from organic groups, halo atoms, and siloxy groups, each Y is an independently selected divalent bridging group between the silicon atoms bonded to platinum, n is 0, 1, 2, or 3, and COD is 1,5-cyclooctadiene.

In formula (I), each $R^1$ is independently selected from organic groups, halogen atoms, and siloxy groups. The term "organic groups" as used herein means groups having carbon chains or rings and the substituents bonded to those carbon chains or rings may include hydrogen atoms, halo atoms and oxygen, where the oxygen may also be connecting two carbon chains or bonded directly to a silicon atom. Preferred organic groups include alkyl groups comprising 1 to 25 carbon atoms, aryl groups comprising 6 to 25 carbon atoms, and oxygen-containing organic groups.

The alkyl groups comprising 1 to 25 carbon atoms of $R^1$ may be linear, branched or cyclic. The alkyl groups may also be unsubstituted or substituted with halo atoms or oxygen groups. Examples of unsubstituted alkyl groups of $R^1$ include methyl, ethyl, isopropyl, butyl, isobutyl, tert-butyl, pentyl, hexyl, dodecyl, octadecyl, cyclopentyl, cyclohexyl, cyclohexylmethyl, 2-cyclohexylethyl, and norbornyl. Examples of substituted alkyl groups of $R^1$ include chloromethyl, 3-chloropropyl, 3,3,3-trichloropropyl, 3,3,3-trifluoropropyl, fluorocyclohexyl, and methoxycyclohexyl. Preferred alkyl groups are methyl, ethyl, and 3,3,3-trifluoropropyl, with methyl and 3,3,3-trifluoropropyl being most preferred.

The aryl groups comprising 6 to 25 carbon atoms of $R^1$ may be unsubstituted or substituted with halo atoms or oxygen groups. Examples of unsubstituted aryl groups of $R^1$ include phenyl, tolyl, xylyl, biphenyl, benzyl, and naphthyl. Examples of substituted aryl groups of $R^1$ include chlorophenyl, methoxyphenyl, and pentafluorophenyl. Preferred aryl groups are phenyl, tolyl, and chlorophenyl.

The oxygen-containing organic groups of $R^1$ are groups having an oxygen radical bonded either directly to a silicon atom, connecting two carbon chains or as a substituent of a carbon chain. Preferred oxygen-containing organic groups include alkoxy groups and acyloxy groups.

The alkoxy groups have a formula described by $-OR^2$, where $R^2$ is an alkyl group comprising 1 to 25 carbon atoms. The alkyl group of $R^2$ may be substituted or unsubstituted. Examples of $R^2$ are as described above for the alkyl groups of $R^1$. Specific examples of alkoxy groups useful in the invention include methoxy, ethoxy, 2-chloroethoxy, tertiarybutoxy, 2,2,2-trifluoroethoxy, pentoxy, cyclohexoxy, methoxyethoxy, bromocyclohexoxy, and methylcyclohexoxy. Preferably, $R^2$ is an alkyl group comprising 1 to 6 carbon atoms.

The acyloxy groups have a formula described by $-O(C=O)-R^3$, where $R^3$ is independently selected from alkyl groups comprising 1 to 25 carbon atoms and aryl groups comprising 6 to 25 carbon atoms. The alkyl groups and aryl groups of $R^3$ can be substituted or unsubstituted. Examples of the alkyl groups comprising 1 to 25 carbon atoms and aryl groups comprising 6 to 25 carbon atoms of $R^3$ are as described above for $R^1$. Specific examples of acyloxy groups useful in the invention include acetoxy, propionyloxy, benzoyloxy, chloroacetoxy, dichloroacetoxy, trichloroacetoxy, and trifluoroacetoxy. Preferably, $R^3$ is an alkyl group comprising 1 to 6 carbon atoms, most preferably $R^3$ is a methyl group.

In formula (I), each $R^1$ may also comprise halo atoms. Examples of these halo atoms include chloro, bromo, fluoro, and iodo atoms. Preferred halo atoms are chloro, bromo and fluoro, with chloro and bromo being most preferred.

Each $R^1$ may also comprise siloxy groups. It is preferred that the siloxy groups have the formula $-(OSiR^4{}_2)_n-X$, where each $R^4$ and X are independently selected from alkyl groups comprising 1 to 25 carbon atoms, aryl groups comprising 6 to 25 carbon atoms, halo atoms, and oxygen-containing organic groups and n is 1 to 6. Examples of the alkyl groups and aryl groups of $R^4$ and X are as described above for $R^1$. Examples of oxygen-containing organic groups are also as described above for $R^1$. Preferred siloxy groups include —$OSiMe_3$, —$OSiMe_2Ph$, —$OSiMe_2CH_2CH_2CF_3$, and —$OSiMe_2OSiMe_3$, where Me means methyl and Ph means phenyl.

It is most preferred that each $R^1$ is independently selected from methyl, phenyl, 3,3,3-trifluoropropyl, and chloro.

In formula (I), each Y group is an independently selected divalent bridging group between the silicon atoms bonded to platinum. This divalent bridging group may be comprised of —$(OSiR^1_2)_m$—O— units, where $R^1$ is as described above and m is from 0 to 3, or divalent hydrocarbon groups comprising 1 to 5 carbon atoms. For example, the bridged siloxy structure may be based on linear siloxanes, cyclic siloxanes or silsesquioxanes, and the bridging hydrocarbon structure may be an alkylene such as —$CH_2CH_2$— or an arylene such as ortho-phenylene.

Subscript n describes how many $R^1$ groups and Y groups are bonded to each silicon atom bonded to platinum. Subscript n is an integer from 0 to 3. Preferably n is 0 or 1.

The other important ingredient of the present invention is COD which is 1,5-cyclooctadiene. The COD is bound to platinum in an eta-4 bonding mode.

Another embodiment of the present invention relates to methods of contacting COD, platinum, and SiH-containing silanes or siloxanes in sufficient amounts to make the alkene-platinum-silyl complexes described by formula (I) $(COD)Pt(SiR^1_{3-n})_2Y_n$, where $R^1$, Y, n, and COD are as described above. These methods include premixing the COD and SiH-containing silane or siloxane prior to the addition of the platinum and premixing the COD and platinum prior to the addition of the SiH-containing silane or siloxane. In each case, the COD and SiH-containing silane or siloxane are added in amounts sufficient to form the alkene-platinum-silyl complex described by formula (I).

The platinum used in the above method can be a metal salt or complex, usually including anionic ligands such as halides or acetates. Examples of the platinum useful in this method include platinum diacetate, bis(acetylacetonate) platinum, $PtCl_2$, $H_2PtCl_6$, $PtCl_4$ and $CODPtCl_2$. Preferred platinum complexes are $PtCl_2$ and $CODPtCl_2$ because of their ease of use. The platinum may be a single species or a mixture of two or more species.

The SiH group can be bonded to a silane molecule or siloxane molecule. There may be one or more SiH groups per silane or siloxane molecule. Examples of SiH-containing silanes useful in the above method include $HSiMeCl_2$, $HSiCl_3$, $ClMe_2SiH$, $PhMe_2SiH$, 1,2-bis-dimethylsilylethane, and 1,2-bis-dimethylsilylbenzene where Me means methyl and Ph means phenyl. Examples of SiH-containing siloxanes useful in the above method include 1,1,3,3,5,5-hexamethyltrisiloxane, pentamethyidisiloxane, $(HSiO_{3/2})_8$, 1,1,2,2-tetramethyidisiloxane, 1,3,5,7-tetramethylcyclotetrasiloxane. The SiH-containing silane or siloxane may be a single species or a mixture of two or more species The amounts of COD, platinum and SiH groups required to make the alkene-platinum-silyl complexes of the present invention will differ depending on what type of platinum is used. Generally, for every anionic ligand (for example halide, acetate etc.) to be removed from platinum there should be at least 1 SiH group added. Two additional SiH groups for each atom of platinum are also needed to meet the compositional requirement of the catalyst structure. The upper limit of SiH groups which can be used will depend on the reaction conditions; however if a several-fold excess is used the alkene-platinum-silyl complex will not form or may be rapidly destroyed. Preferably, the minimum number of SiH groups needed is the number of anionic ligands on platinum to be removed as silane (as opposed to a non-reactive salt) plus 2. Therefore, if using $PtCl_2$ or $CODPtCl_2$ at least 4 SiH groups are required for each $PtCl_2$ or $CODPtCl_2$ molecule, preferably 4 SiH groups on the same basis. If the alkene-platinum-silyl complexes is to be made in situ during a hydrosilation reaction, then it is not necessary to separately add SiH groups for every anionic ligand on platinum because the catalyst forms in-situ from the SiH groups of the silane added and then starts the hydrosilation catalysis of the alkene with the further SiH added.

The amount of COD added to the reaction mixture is critical in that there always must be close to at least 3 moles COD added for each mole of platinum. The total amount of COD required is determined partly by the amount of SiH used, since for every SiH used to remove an anionic ligand, the H component must be removed via hydrogenation. Preferably, there should be from 3 to 20 moles of COD added for each mole of platinum, the upper limit of COD is only determined by any detrimental effect of the excess COD on catalyst activity in hydrosilation. Some of the COD may be added to the mixture already bonded to platinum, for example, if added as $(COD)PtCl_2$, or it could all be added as a separate component.

The order of addition of the ingredients COD, platinum and SiH-containing silanes or siloxanes is important to the formation of the alkene-platinum-silyl complexes. Generally, when the SiH-containing silane or siloxane contacts platinum, the COD must also be present. However, it is not critical whether the COD and SiH-containing silane or siloxane are premixed prior to addition to the platinum or whether the COD and platinum are premixed prior to the addition of the SiH-containing silane or siloxane. The preferred order of addition for preparing the alkene-platinum-silyl complexes of the present invention is the addition of the SiH-containing silane or siloxanes to a mixture of platinum and COD.

The contacting of the ingredients is by any method known in the art. Preferably, the contacting is by mixing with a mechanical stirrer or mixer. The contacting is preferably done with the reactants in a suitable solvent, although a neat reaction may be feasible. The solvent can be polar or non-polar, but polar solvents are preferred for faster reaction. Solvents which are known to complex with platinum, or that are discovered to complex with platinum should be avoided. Examples of suitable solvents include benzene, toluene, dichloromethane, chloroform, and 1,2-dichloroethane.

The temperature that the reaction is run at is not critical provided each of the reactants remains in the mixture. However, it should be understood that different SiH-containing silanes or siloxanes react under different conditions of temperature, pressure or solvent. Generally, the reaction can be run at temperatures from about 20° C. to 100° C. and temperatures from 32° C. to 70° C. are preferred. If necessary to ensure the reactants remain in the mixture at the temperature the reaction is being run, pressure can also be added.

A preferred alkene-platinum-silyl complex described by Formula (I) where n is 0 may be prepared as follows:

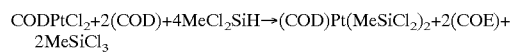

where COD is as described above, Me is methyl, and COE is cyclooctene. Although not wanting to be tied to any theory, the inventors believe the two key reactions in the above process are removal of chloride from platinum as chlorosilane and removal of the H from SiH via hydrogenation of COD.

The alkene-platinum-silyl complexes of the present invention are useful as catalysts for hydrosilation reactions. The alkene-platinum-silyl complex can be added separately to the reaction mixture or formed in situ during the hydrosilation reaction.

Generally, hydrosilation products can be made by mixing ingredients comprising (A) at least one silane or siloxane having at least one non-aromatic, carbon-carbon multiple bond or at least one organic material having at least one non-aromatic, carbon-carbon multiple bond; (B) at least one silane or siloxane having at least one SiH group; and (C) an alkene-platinum-silyl complex described by formula (I) $(COD)Pt(SiR^1_{3-n})_2Y_n$, where $R^1$, Y, n and COD are as described above.

There are many methods which can be utilized to form the alkene-platinum-silyl complex in situ during a hydrosilation reaction. For example, one could mix COD, platinum, and at least one silane or siloxane having at least one non-aromatic, carbon-carbon multiple bond or at least one organic material having at least one non-aromatic, carbon-carbon multiple bond, and then add to the premix at least one silane or siloxane having at least one SiH group.

Another in situ method includes mixing COD, at least one silane or siloxane having at least one SiH group, and at least one silane or siloxane having at least one non-aromatic, carbon-carbon multiple bond or at least one organic material having at least one non-aromatic, carbon-carbon multiple bond, and then adding the platinum to the premix.

A further in situ method includes mixing platinum, at least one silane or siloxane having at least one SiH group, and at least one silane or siloxane having at least one non-aromatic, carbon-carbon multiple bond or at least one organic material having at least one non-aromatic, carbon-carbon multiple bond, and then adding COD to the premix.

With each of these methods the order of addition of each of the ingredients forming each premix is critical in that the silane or siloxane having at least one non-aromatic, carbon-carbon multiple bond or at least one organic material having at least one non-aromatic, carbon-carbon multiple bond must be present before or at the same time as the silane or siloxane having at least one SiH group is mixed with platinum. However, when the catalyst forms in situ during a hydrosilation reaction, it is not necessary to add SiH-containing groups separate from the SiH-containing silane or siloxane used for the hydrosilation.

The SiH-containing silanes and siloxanes, the silanes or siloxanes having at least one non-aromatic, carbon-carbon multiple bond, and the organic materials having non-aromatic, carbon-carbon multiple bonds useful in these hydrosilation reactions can include any of such materials known in the art.

EXAMPLES

The following Examples are merely illustrative and are not intended to limit the invention. As used herein Me is methyl, COD is 1,5-cyclooctadiene

Example 1

Preparation of $(COD)Pt(SiMeCl_2)_2$

A 100 mL, 3-neck, 14/20RB flask, equipped with Teflon sleeves, water condenser, dropping funnel, and Teflon stirring bar was charged with $Pt(COD)Cl_2$ (0.015 mol, 5.61 g, Johnson-Matthey, N.J.) and evacuated for 10 min at 1–2 mm Hg. The flask was backfilled with dry nitrogen. COD (5.5 mL, 0.045 mol, Aldrich Chemical, WI) and sieve dried $CDCl_3$ (10 mL, ISOTEC, Inc., OH) were then added to the flask via syringe. Methyldichlorosilane (6.6 mL, 0.0612 mol, Dow Corning, MI) was transferred to the dropping funnel and diluted with 5 mL $CDCl_3$. The flask was heated with a water or silicone fluid bath to 60–65° C. and the methyldichlorosilane was added over 10 min to the stirring slurry in the flask. The funnel was rinsed with 2 mL $CDCl_3$. The mixture was heated at 72–75° C. until it became completely transparent and clear (30–45 min). The bath temperature was then quickly dropped to 48–50° C. and the mixture heated at this temperature for 2–3 hr, midway through which a white precipitate containing the product $(COD)Pt(SiMeCl_2)_2$ forms (depending on concentration in $CDCl_3$). The mixture was then stirred overnight at 30–32° C. Complete conversion to product was achieved (as evidenced from $^1H$, $^{13}C$, $^{29}Si$, and $^{195}Pt$ NMR analysis which provide characteristic signals for this compound. In addition, X-ray crystal structure analysis also characterized the platinum complex) and the solution or the solid complex is ready at this point for use as a catalyst. Regular chloroform (that is $CHCl_3$) can readily be substituted for the deuteriochloroform ($CDCl_3$) for the preparation of the complex, provided the regular chloroform is unstabilized or stabilized with amylenes and not with an alcohol which will react with Si—Cl bonds and may also otherwise destroy the complex.

Further purification of the catalyst was carried out as follows. Anhydrous hexanes (30 mL, Aldrich Chemical) were added to the flask and the mixture stirred at −78° C. for one hour to facilitate complete precipitation of $(COD)Pt(SiMeC)_2)_2$. The off-white solid was filtered cold and washed with three 12–15 mL portions of dry hexanes. The microcrystalline solid on the filter was dried under vacuum and transferred back to the original flask. Crude yield of product: 94–95%. If desired, the crude solid may now be further purified via dissolution in $CDCl_3$ (or $CHCl_3$) (30 mL, heating to 30–35° C.) containing added COD at 1–1.5 mol COD/mol Pt, a second filtration (and washing with 5–10 mL $CDCl_3$), followed by recrystallization via storage in a freezer at −20° C., to yield colorless crystals of pure $Pt(COD)(SiMeCl_2)_2$.

Catalysis Examples

In order to demonstrate that the above compound is the actual active catalyst (in its resting state, ready to begin catalytic cycles without the need for activation steps), first a stoichiometric hydrosilylation of 1-hexene was carried out with the above compound, followed by catalytic hydrosilylation at 50 ppm Pt level.

Example 2

Reaction between 1-hexene and $MeSiHCl_2$ in the Presence of a Stoichiometric Level of $(COD)Pt(SiMeCl_2)_2$ A solution of the above $(COD)Pt(SiMeCl_2)_2$ complex containing 0.005 mol complex in 18 mL $CDCl_3$ was prepared as described above in Example 1 and an aliquot containing 0.0014 mol complex (and by products cyclooctene, $MeSiCl_3$ and excess COD) was cannulated to a Si-free Teflon NMR tube. 1-hexene (350 µL, 0.0028 mol, Aldrich Chemical) was added followed by $MeSiHCl_2$ (302 µL, 0.0029 mol, Dow Corning) and the mixture heated in the NMR probe at 50° C. NMR analysis after about 4 hours indicated complete hydrosilylation of the 1-hexene to n-hexylmethyldichlorosilane, with no isomerization of I-hexene and, more importantly, no loss of the 0.0014 mol Pt complex to any reaction with the substrates or the product. The complex (COD)Pt(SiMeCl$_2$)$_2$ remained structurally unchanged while 1-hexene was hydrosilylated to n-hexylmethyldichlorosilane.

Example 3

Reaction between 1-hexene and MeSiHCl$_2$ in the Presence of a Catalytic Level of (COD)Pt(SiMeCl$_2$)$_2$ Since it was possible that a catalytic amount of another Pt complex in the above reaction and not the named compound was responsible for the observed catalysis, the following reaction was carried out to eliminate that possibility.

A 100 mL, 3-neck flask equipped with a Teflon stirring bar, addition funnel and water condenser was purged with nitrogen and charged with 1-hexene (12.5 mL, 0.10 mol). MeSiHCl$_2$ (ca. 11.0 mL, 0.102 mol) was transferred to the additional funnel. An aliquot of the above "stoichiometric" reaction mixture containing 50 ppm mol Pt as (COD)Pt (SiMeCl$_2$)$_2$ with respect to 1-hexene (from Example 2) was added to the 1-hexene in the flask using a microliter syringe. The flask was heated to 60° C. and the silane added over 20 min. The hydrosilylation reaction began within 3–5 minutes and was essentially over at the end of the silane addition, as evidenced by the lack of any refluxing of unreacted silane (b.p. 41° C.) in the flask. The light yellow solution was heated for another 30 min, following which NMR analysis showed complete hydrosilylation, with no trace of residual 1-hexene or 2-hexene (isomerization). The solution remained yellow and without the precipitation of any platinum for several weeks.

Since a homogeneous Pt complex can be typically detected at close to 1% levels by NMR, it is clear that the above aliquot containing 50 ppm mol of the described complex, would contain less than about 0.5ppm mol of another homogeneous Pt complex (no other homogeneous species was evident by NMR). At this low level, catalysis of the 1-hexene hydrosilylation by such a second species would be extremely slow, unlike the fast rate of hydrosilylation that was actually observed. Thus, the (COD)Pt(SiMeCl$_2$)$_2$ complex described above is a true, active hydrosilylation catalyst.

We claim:

1. Alkene-platinum-silyl complexes described by formula (I)

(COD)Pt(SiR$^1_{3-n}$)$_2$Y$_n$, where each R$^1$ is independently selected from organic groups, halo atoms, and siloxy groups, each Y is an independently selected divalent bridging group between the silicon atoms bonded to platinum, n is 0, 1, 2, or 3, and COD is 1,5-cyclooctadiene.

2. The alkene-platinum-silyl complexes of claim 1 where the organic groups of R$^1$ are independently selected from alkyl groups comprising 1 to 25 carbon atoms, aryl groups comprising 6 to 25 carbon atoms, and oxygen containing organic groups.

3. The alkene-platinum-silyl complexes of claim 2 where the alkyl groups of R$^1$ are independently selected from methyl, ethyl, and 3,3,3-trifluoropropyl.

4. The alkene-platinum-silyl complexes of claim 2 where the aryl groups of R$^1$ are independently selected from phenyl, tolyl, and chlorophenyl.

5. The alkene-platinum-silyl complexes of claim 2 where the oxygen-containing organic groups of R$^1$ are independently selected from alkoxy groups and acyloxy groups.

6. The alkene-platinum-silyl complexes of claim 1 where the halo atoms of R$^1$ are independently selected from chloro, bromo and fluoro.

7. The alkene-platinum-silyl complexes of claim 1 where the siloxy groups of R$^1$ are selected from the formula —(OSiR$^4_2$)$_n$—X, where each R$^4$ and X are independently selected from alkyl groups comprising 1 to 25 carbon atoms, aryl groups comprising 6 to 25 carbon atoms, halo atoms, and oxygen-containing organic groups and n is 1 to 6.

8. The alkene-platinum-silyl complexes of claim 1 where each R$^1$ is independently selected from methyl, phenyl, 3,3,3-trifluoropropyl, and chloro.

9. The alkene-platinum-silyl complexes of claim 1 where each Y is independently selected from (OSiR$^1_2$)$_m$—O— units or divalent hydrocarbon groups comprising 1 to 5 carbon atoms where each R$^1$ is independently selected from organic groups, halogen atoms, and siloxy groups and m is from 0 to 3.

10. The alkene-platinum-silyl complexes of claim 8 where each Y is independently selected from (OSiR$^1_2$)$_m$—O— units or divalent hydrocarbon groups comprising 1 to 5 carbon atoms where each R$^1$ is independently selected from organic groups, halogen atoms, and siloxy groups and m is from 0 to 3.

11. A method of preparing alkene-platinum-silyl complexes described by formula (I)

(COD)Pt(SiR$^1_{3-n}$)$_2$Y$_n$, comprising the steps of
(a1) mixing COD and platinum to form a premix, and
(b1) adding SiH-containing silanes or siloxanes to the premix, or
(a2) mixing COD and SiH-containing silanes or siloxanes to form a premix, and
(b2) adding the premix to platinum,
where the COD and SiH-containing silanes or siloxanes are added in amounts sufficient to form the complex described by formula (I), where each R$^1$ is independently selected from organic groups, halo atoms, and siloxy groups, Y is a divalent bridging group between the silicon atoms, and COD is 1,5-cyclooctadiene.

12. The method of claim 11 where the platinum comprises CODPtCl$_2$, at least 2 additional moles of COD are added per one mole of CODPtCl$_2$ and at least 4 SiH groups are added per one molecule of CODPtCl$_2$.

13. The method of claim 12 where an additional 2 to 19 moles of COD is added for every one mole of CODPtCl$_2$.

14. The method of claim 12 where 4 SiH groups are added per one molecule of CODPtCl$_2$.

15. A method of hydrosilating a compound having at least one non-aromatic, carbon-carbon multiple bond comprising
(IA) mixing COD, platinum, and at least one silane or siloxane having at least one non-aromatic, carbon-carbon multiple bond or at least one organic material having at least one non-aromatic, carbon-carbon multiple bond to form a hydrosilation premix-A;
(IIA) adding to the hydrosilation premix-A at least one silane or siloxane having at least one SiH group,
such ingredients being added in amounts sufficient to provide at least 3 moles of COD for every one mole of platinum and at least 1 SiH group for each non-aromatic, carbon-carbon multiple bond, where COD is 1,5-cyclooctadiene.

16. The method of claim 15 where the platinum is CODPtCl$_2$ and at least 2 additional moles of COD are added for every one mole of CODPtCl$_2$.

17. A method of hydrosilating a compound having at least one non-aromatic, carbon-carbon multiple bond comprising (IB) mixing COD, at least one silane or siloxane having at least one non-aromatic, carbon-carbon multiple bond or at least one organic material having at least one non-aromatic, carbon-carbon multiple bond, and at least one silane or siloxane having at least one SiH group to form a hydrosilation premix-B;

(IIB) adding platinum to the hydrosilation premix-B, such ingredients being added in amounts sufficient to provide at least 3 moles of COD for every one mole of platinum and at least 1 SiH group for each non-aromatic, carbon-carbon multiple bond, where COD is 1,5-cyclooctadiene.

18. A method of hydrosilating a compound having at least one non-aromatic, carbon-carbon multiple bond comprising (IC) mixing platinum, at least one silane or siloxane having at least one non-aromatic, carbon-carbon multiple bond or at least one organic material having at least one non-aromatic, carbon-carbon multiple bond, and at least one silane or siloxane having at least one SiH group to form a hydrosilation premix-C;

(IIC) adding COD to the hydrosilation premix-C, such ingredients being added in amounts sufficient to provide at least 3 moles of COD for every one mole of platinum and at least 1 SiH group for each non-aromatic, carbon-carbon multiple bond, where COD is 1,5-cyclooctadiene.

* * * * *